United States Patent [19]

Yamaguchi et al.

[11] Patent Number: 5,705,373
[45] Date of Patent: Jan. 6, 1998

[54] PRODUCTION OF 2-KETO-L-GULONIC ACID USING PSEUDOGLUCONOBACTER SACCHAROKETOGENES WITH RECYCLING

[75] Inventors: Takamasa Yamaguchi; Kenkichi Yoneto, both of Kobe; Giichi Tanaka, Kawabe-gun, all of Japan

[73] Assignee: Takeda Chemical Industries, Ltd., Osaka, Japan

[21] Appl. No.: 682,258

[22] Filed: Jul. 16, 1996

Related U.S. Application Data

[63] Continuation of Ser. No. 359,652, Dec. 20, 1994, abandoned.

[30] Foreign Application Priority Data

Dec. 24, 1993 [JP] Japan ................ 5-328392

[51] Int. Cl.$^6$ .............. C12P 39/00; C12P 7/60
[52] U.S. Cl. ..................... 435/138; 435/42
[58] Field of Search ................... 435/42, 138

[56] References Cited

U.S. PATENT DOCUMENTS

| | | | |
|---|---|---|---|
| 4,278,764 | 7/1981 | Rottigni et al. | 435/144 |
| 4,877,735 | 10/1989 | Nogami et al. | 435/138 |
| 4,960,695 | 10/1990 | Hoshino et al. | 435/42 |
| 5,085,993 | 2/1992 | Fujiwara et al. | 435/138 |
| 5,312,741 | 5/1994 | Hoshino et al. | 435/42 |

FOREIGN PATENT DOCUMENTS

| | | |
|---|---|---|
| 221707 | 10/1985 | European Pat. Off. |
| 3112989 | 5/1988 | Japan. |
| 5-503635 | 6/1993 | Japan. |

OTHER PUBLICATIONS

Kennedy et al. in Applied Biochemistry and Bioengineering vol. 4 Immobilized Microbial Cells, pp. 236–245 (1983).
Yukawa et al., Nippon Nogerkagaku Kaishi, vol. 59, No. 1, pp. 31–37 (1985).

*Primary Examiner*—Sandra E. Saucier
*Attorney, Agent, or Firm*—Wenderoth, Lind & Ponack

[57] ABSTRACT

A method for producing 2-keto-L-gulonic acid (hereinafter referred to as 2KGA) which comprises (1) culturing a microorganism capable of producing 2KGA from L-sorbose, in a liquid culture medium containing a substrate to produce 2KGA and (2) recovering the produced 2KGA, while recovering the microorganism in the culture broth, (3) inoculating the recovered microorganism to a new liquid culture medium for the following culture and (4) repeating said culture and recovering at least once.

The present invention provides an industrially advantageous, versatile method for producing 2KGA that shortens the overall culture time, and reduces the amounts of starting medium materials and culture waste.

5 Claims, No Drawings

PRODUCTION OF 2-KETO-L-GULONIC ACID USING PSEUDOGLUCONOBACTER SACCHAROKETOGENES WITH RECYCLING

This application is a continuation of now abandoned application Ser. No. 08/359,652, filed Dec. 20, 1994, now abandoned.

The present invention relates to an improved method for producing 2-keto-L-gulonic acid (hereinafter referred to as 2KGA) which comprises (1) culturing a microorganism capable of producing 2KGA from L-sorbose, in a liquid culture medium containing a substrate to produce 2KGA and (2) recovering the produced 2KGA, while recovering the microorganism in the culture broth, (3) inoculating the recovered microorganism to a new liquid culture medium for the following culture and (4) repeating said culture and recovering at least once so as to shorten the time for the next culture and increase production efficiency.

The present invention is applicable to microbial cell reactions, including fermentation, for production of 2KGA from a wide variety of substrates.

The method of the present invention is advantageously applicable to the industrial production of 2-keto-L-gulonic acid, a useful intermediate for the synthesis of L-ascorbic acid using microorganisms.

Traditionally, 2-keto-L-gulonic acid, a useful intermediate for the synthesis of L-ascorbic acid, has been produced by an industrially well-established process known as Reichstein's method (see Helvetica Chimica Acta, Vol. 17, p. 311, 1934). However, this method is unsatisfactory for a modern industrial technology, because of the large number of steps and the usage of the large amount of organic solvents.

As substitutes for Reichstein's method, some methods, mainly those using microorganisms, have been proposed, including the method in which D-glucose is microbially oxidized to 2,5-diketo-gluconic acid, which is then microbially or chemically reduced to 2KGA (see Japanese Patent Examined Publication Nos. 14493/1964, 25033/1978, 15877/1981 and 35920/1984), the method which comprises introducing the 2,5-diketo-D-gluconic acid reductase gene of Corynebacterium into Erwinia which is capable of producing 2,5-diketo-D-gluconic acid according to DNA recombination technique to obtain 2KGA from D-glucose by a one-step fermentation process (Science, Vol. 230, p. 144, 1985), and the method in which D-sorbitol or L-sorbose, as the starting material, is oxidized using a bacterium of the genus Gluconobacter, to yield 2KGA (see Japanese Patent Unexamined Publication No. 150287/1990).

There is another known method, in which L-sorbose is efficiently converted into 2KGA using a microorganism of the genus Pseudogluconobacter isolated from soil (see Japanese Patent Unexamined Publication No. 228288/1987). Also, European Patent Application Publication No. 221707 (Japanese Patent Unexamined Publication No. 85088/1989) discloses a more efficient method of 2KGA production from L-sorbose using the above-mentioned microorganism of the genus Pseudogluconobacter, developed on the basis of the finding that 2KGA production by said microorganism is markedly promoted by the addition of rare earth elements to the medium.

Despite various attempts at improving productivity in the production of valuable substances by microbial cell reactions, there has been no industrially advantageous cell reaction method or fermentation method that significantly reduces the amounts of starting medium materials and culture wastes and shortens operation time, such as that for culture, with simple versatile equipment.

In any of the above-described known methods of 2KGA production, an ordinary culture method known as batch culture is used. Specifically, the substrate sugar or sugar alcohol is added to the medium all at once at culture initiation, or some or all of the substrate is semi-continuously or continuously added to the medium during culture, and culture is stopped when enough 2KGA has been accumulated and efficient conversion to 2KGA no longer occurs even if culture is continued, to obtain a culture broth. The cells removed from the culture system in the process that follows are usually wasted; the next cycle of culture is begun at seed culture. However, those methods require seed culture in each culturing cycle, normally using a dense medium because of the requirement for microbial proliferation or growth in the main culturing process. These aspects are uneconomical from the viewpoint of industrial productivity. Also, a large amount of culture waste is produced in separation of the desired product after completion of culture, which is undesirable from the viewpoint of environmental protection. Also, much time is taken to proliferate the microorganism to the desired amount of cells in the main culturing process, because the amount of inoculation for main culture of the seed obtained by seed culture is very small, thus extending the time required for the main culturing process.

As a solution to these problems, the immobilized cell method and the immobilized enzyme method have been proposed, in which microbial cells or an enzyme involved in the desired reaction are immobilized to a carrier. However, these methods invariably require much effort to achieve satisfactory immobilization or retain the activity of the microbial cells or enzyme. In recent years, the bioreactor has been developed, which uses a combination of fermentor and filtering membrane to perform culture. However, the bioreactor has some drawbacks, including equipment complexity and general operational difficulty, requiring high cost and sophisticated technology to prevent germ contamination of the equipment.

The object of the present invention is to provide an industrially advantageous method that is applicable to a wide variety of culture or microbial cell reactions for the production of 2KGA, and that significantly reduces the amounts of starting medium materials and culture wastes and shortens operation time, such as that for culture, with simple versatile equipment.

With this situation in mind, the present inventors tried various improvements in search of a more advantageous method of microbial cell reaction. The inventors attempted a method of 2KGA fermentation wherein microbial cells are grown in a single cycle of culture to obtain the desired product 2KGA, present in the aqueous portion of the culture broth or microbial cell reaction broth, after which the cells are again used in the next cycle of 2KGA fermentation with their activity retained, rather than wasted. As a result, the inventors found it possible to markedly shorten fermentation time and reduce the amount of starting medium materials and culture wastes, for the same amount of substrate oxidized, in comparison with ordinary batch culture and other methods, by the recycling culture method, in which some or all of the thus-obtained cells is used in the next cycle of culture, preferably by adding an activity retention aid. The inventors made further investigations based on this finding, and developed the present invention.

Accordingly, the present invention relates to a method for producing 2-keto-L-gulonic acid (hereinafter referred to as 2KGA) which comprises (1) culturing a microorganism capable of producing 2KGA from L-sorbose, in a liquid culture medium containing a substrate to produce 2KGA and (2) recovering the produced 2KGA, while recovering the microorganism in the culture broth, (3) inoculating the recovered microorganism to a new liquid culture medium for the following culture and (4) repeating said culture and recovering at least once.

Specifically, the present invention includes a method for producing 2KGA comprising culture or microbial cell reaction primarily by using at least one microorganism capable of producing 2KGA, wherein cells are repeatedly used in two or more cycles with the necessary activity retained, while or after the produced 2KGA is separated and recovered.

Here, the culture or microbial cell reaction may be one in which a microorganism having the desired production capability is cultured or otherwise treated to obtain a sufficient number of cells thereof, which are then brought into contact with a substrate, with or without cell proliferation at the time of cell contact with the substrate. The microbial cell reaction may also be carried out by an ordinary culturing method, in which a seed obtained by small-scale seed culture is transferred to a main medium to produce the desired product with cell proliferation, especially in the first cycle of culture. More specifically, the present invention relates to a culturing method wherein after culturing proceeds and 2KGA is produced, the cell portion containing the medium solids and the aqueous portion containing 2KGA are separated from the culture broth or cell reaction broth using a separating means, such as a membrane or centrifuge, and the thus-obtained cell portion is repeatedly used in the next cycle of batch culture or microbial cell reaction, preferably using a new medium. In this case, in inoculating the viable microbial cells separated from the culture broth, preferably after completion of the reaction, to the next medium, a commonly used method may be employed to bring the viable cells in contact with the medium. In the present specification, "fermentation for producing 2KGA as the final product" is also referred to as briefly "2KGA fermentation," and "microbial cell reaction broth" may include "culture broth." "Culture in which cells are repeatedly used" is also referred to as "recycling culture."

The method of the present invention is applicable to a variety of substrates and microorganisms.

The substrate for the present method is preferably a sugar or a sugar alcohol. Example of substrates include L-sorbose, D-glucose and D-sorbitol. L-Sorbose is the most preferred substrate for the methods using some microorganisms.

The microorganism for the present invention is preferably a bacterium. More specifically, there may be mentioned bacteria of the genus Pseudogluconobacter, Gluconobacter, Pseudomonas, Corynebacterium, Acetobacter, and Erwinia as the preferred bacteria.

The present invention is hereinafter described more specifically. The microorganism for the present invention, capable of producing 2KGA, is exemplified by known microorganisms of the genus Pseudogluconobacter, Pseudomonas, Gluconobacter, Acetobacter or Corynebacterium, and microorganisms of the genus Erwinia incorporating the 2,5-diketo-D-gluconic acid reductase gene. In addition to these microorganisms, any microorganism can be used for the present invention, as long as it is capable of producing 2KGA. In fermentation with L-sorbose as the substrate, in particular, microorganisms of the genus Pseudogluconobacter and Gluconobacter are preferably used. More preferred are the microorganisms of the genus Pseudogluconobacter. Example microorganisms of the genus Pseudogluconobacter include *Pseudogluconobacter saccharoketogenes* strains K591s ( FERM BP-1130), 12-5 (FERM BP-1129), TH14-86 (FERM BP-1128), 12-15 (FERM BP-1132), 12-4 (FERM BP-1131) and 22-3 (FERM BP-1133).

In the culture of the present invention, culturing conditions, such as medium composition and culturing temperature, may be adjusted as appropriate to the strain used. For example, in 2KGA fermentation using a bacterium of the genus Pseudogluconobacter, the culturing method, medium composition and culturing conditions described in EP-B-0221707 [Japanese Patent Unexamined Publication (JP-A) No. 228288/1987] can be used. As described in the same patent publication, fermentation is facilitated when the microorganisms of the genus Pseudogluconobacter are subjected to culture in which the microorganisms capable of producing 2KGA are cultured in the presence of an concomitant microorganism capable of supplying a growth factor to the microorganisms capable of producing 2KGA (hereinafter sometimes referred to as mixed culture). Examples of such concomitant microorganisms to be used in mixed culture include microorganisms of the genus Bacillus, Pseudomonas, Proteus, Citrobacter, Enterobacter, Erwinia, Xanthomonas and Flavobacterium.

As the specific species that are allowed to be present concomitantly, the following may be mentioned.

*Bacillus cereus* IFO 3131

*Bacillus licheniformis* IFO 12201

*Bacillus megaterium* IFO 12108

*Bacillus pumilus* IFO 12090

*Bacillus amyloliquefaciens* IFO 3022

*Bacillus subtilis* IFO 13719

*Bacillus circulans* IFO 3967

*Pseudomonas trifolii* IFO 12056

*Pseudomonas maltophilia* IFO 12692

*Proteus inconstans* IFO 12930

*Citorobacter freundii* IFO 13544

*Enterobacter cloacae* IFO 3320

*Erwinia herbicola* IFO 12686

*Xanthomonas pisi* IFO 13556

*Xanthomonas citri* IFO 3835 and

*Flavobacterium menigosepticum* IFO 12535.

For such mixed culture, it is particularly preferable to use a microorganism of the genus Bacillus. Mixed culture in the presence of the above-mentioned microorganisms is also preferable in a method using a microorganism of the genus Gluconobacter. When a microorganism of the genus Pseudogluconobacter is used, it is preferable to use a liquid medium containing sucrose, and ammonium sulfate and/or urea.

Concerning the culturing means for the method of the present invention, a known culturing means, such as shaking culture, standing culture or aerated-agitated culture, can be used according to the microorganism used and the purpose of culture.

Microbial cells of the microorganisms in the culture broth can be recovered using apparatuses in common use for removing cells from the culture broth. Such apparatuses include hollow fiber membrane filters, ceramic membrane filters and centrifuges. These apparatuses may be used singly or in combination. Two or more kinds of apparatuses may be used in combination. The centrifuge, if used, is preferably a continuous centrifuge, capable of continuously treating the culture broth. It is desirable that the apparatus be used in a partially or totally sterile condition.

Concerning these apparatuses, ordinary commercially available apparatus may be used as such, or with partial modifications as necessary.

The appropriate type of apparatus is chosen depending on the amounts of cells and solids in the culture broth. The capacity and number of apparatuses are determined mainly on the basis of culture broth volume. The cells are recovered at the rate of over 25%, preferably 50–100% of the culture broth. The temperature at the time of cell recovery is normally 0°–50° C., preferably 5°–40° C.

Microorganisms, specifically cells thereof, can be used repeatedly without limitation, as long as their capability of producing the desired product, 2KGA, is retained. In the case of 2KGA production using a microorganism of the genus Pseudogluconobacter, microorganisms can be used repeatedly in at least two cycles, normally 4–5 cycles or more.

In the method of microbial cell reaction of the present invention, it is preferable to add a cell reactivity retention aid to the main culture medium so as to retain the reactivity, i.e., productivity for the desired product, of viable cells, over an extended period of time. It is effective to use a naturally-occurring organic nutrient as an activity retention aid, such as yeast extract, dry yeast and/or corn steep liquor (hereinafter also referred to as CSL).

The desired product produced and accumulated in the culture broth or cell reaction broth after the first cycle of main culture and the second and, if desired, the following cycles of recycling culture can be separated and purified by known means based on the properties thereof. For example, 2KGA may be separated as a free acid, or as a salt of sodium, potassium, calcium, ammonium, or the like.

Any method of separation can be used, as long as the purpose of separation is not interfered with. For example, the method in which cells are separated from the reaction product as necessary by filtration, centrifugation, activated charcoal treatment, or the like, after which this solution is directly concentrated, the resulting crystal being collected by filtration and recrystallized to separate the desired product, resin adsorption, chromatography, and salting-out. These methods may be used singly, in combination, or in cycles.

In the case of a microbial cell reaction for 2KGA production, the product, when obtained as a free form, may be converted into a salt of sodium, potassium, calcium, ammonium, or the like, by an appropriate method. When the product is obtained as a salt, it may be converted into a free form or another salt by an appropriate method.

The present invention provides an industrially more economical, efficient and advantageous method of microbial cell reaction for producing 2KGA, that does not require seed culture in each cycle of microbial cell reaction because of the recycling use of cells, shortens cell proliferation in the main microbial cell reaction, and reduces the amounts of starting medium materials and culture waste.

The present invention is hereinafter described in more detail by means of the following examples, which are not to be construed as limitative.

2KGA was quantified by high performance liquid chromatography under the conditions shown below. HPLC assay conditions:

Column: SCR 101H, 7.9×300 mm (produced by Shimadzu Corporation)
Mobile phase: 4 mM sulfuric acid
Detector: RI detector

EXAMPLE 1

TABLE 1

| Slant medium (g/l) | |
|---|---|
| Sorbitol | 25 |
| Peptone | 10 |
| Yeast extract | 10 |
| $CaCO_3$ | 2 |
| Agar | 20 |

TABLE 2

| Seed medium A (g/l) | |
|---|---|
| Lactose | 10 |
| Yeast extract | 10 |
| CSL | 30 |
| Ammonium sulfate | 3 |
| pH | 7.0 |

TABLE 3

| Seed medium B (g/l) | |
|---|---|
| Sucrose | 40 |
| Cottonseed flour | 40 |
| $K_2HPO_4$ | 6.5 |
| $KH_2PO_4$ | 5.5 |
| NaCl | 0.5 |
| Ammonium sulfate | 0.5 |
| $MgSO_4 \cdot 7H_2O$ | 0.05 |
| Calcium pantothenate | 0.25 |
| pH | 7.0 |

TABLE 4

| Fermentation medium (g/l) | |
|---|---|
| Corn steep liquor | 20 |
| Ferrous sulfate | 1 |
| Ammonium sulfate | 3 |
| Sucrose | 0.5 |
| Riboflavin | 0.001 |
| Actcol (produced by Takeda Chemical Industries) | 0.15 |
| Crude rare earth chloride (produced by Mitsubishi Kasei) | 0.1 |
| pH | 7.0 |

TABLE 5

| | Recycling medium (g/l) | | | |
|---|---|---|---|---|
| | A | B | C | D |
| Sucrose | 0.5 | 0.5 | 0.5 | 0.5 |
| Ammonium sulfate | 3 | 3 | 3 | 0.3 |
| CSL (produced by Oji Corn Starch) | | 4 | 4 | |
| Urea | | | | 3 |
| Dry yeast (produced by BEL, France) | | | 5 | |
| Yeast extract (produced by OHLY, Germany) | | | | 1 |

20 ml of seed medium A, having the composition shown in Table 2, was placed in a 200 ml conical flask, and sterilized at 120° C. for 20 minutes. To this flask, a loopful of cells of *Pseudogluconobacter saccharoketogenes* K591s strain (IFO 14464, FERM BP-1130, hereinafter also referred to as the oxidizing bacterium), grown at 30° C. for 3 days on a slant medium of the composition shown in Table 1, was inoculated, followed by shaking culture at 28° C. for 1 day, to yield a first seed culture broth. Similarly, 20 ml of seed medium A was placed in a 200 ml of conical flask, and sterilized. To this flask, 1 ml of the first seed culture broth was inoculated, followed by shaking culture at 28° C. for 2 days, to yield a second culture broth. Separately, to a sterilized 200 ml conical flask containing 20 ml of seed medium B, one loopful of cells of *Bacillus megaterium* (IFO 12108), grown on a slant medium of the composition shown in Table 1, was inoculated, followed by shaking culture at 28° C. for 2 days, to yield a seed culture broth of *Bacillus megaterium* (hereinafter also referred to as the concomitant bacterium).

10 ml of a sterilized double length fermentation medium (sterilized with steam at 120° C. for 20 minutes), consisting of the components shown in Table 1, 5 ml of consisting of 0.8 g of $CaCO_3$ (Shiraishi Calcium Kaisha, Ltd.) (separately sterilized) and 5 ml of consisting of 2 g of L-sorbose (separately sterilized), were dispensed to a 200 ml conical flask. To this flask, 2 ml of the second seed culture broth of the above-described oxidizing bacterium and 1 ml of the seed culture broth of the concomitant bacterium were transferred, followed by shaking culture at 30° C. By 28 hours after fermentation initiation, all L-sorbose had been completely consumed, resulting in accumulation of 1.76 g of 2KGA in the culture broth. The entire amount of this culture broth was aseptically transferred to a previously sterilized centrifugal tube, and centrifuged at 3,000 rpm and 20° C. for 10 minutes using a rotary microcentrifuge with a cooling apparatus. 10 ml of each of media from A to D shown in Table 5 (hereinafter also referred to as recycling medium) was added to a 200 ml conical flask and sterilized. To this flask, 2 g (5 ml) of L-sorbose and 0.8 g (5 ml) of calcium carbonate, both separately sterilized, were added. To this mixture, the entire amount of cells (including other solid contents) obtained by the above centrifugation was aseptically inoculated, followed by shaking culture under the same conditions as in the first shaking culture. This culture is hereinafter referred to as recycling culture.

Recycling culture was repeated in three cycles. Fermentation was stopped when almost all L-sorbose was converted into 2KGA. It took about 1 hour from completion of recycling culture to initiation of the next culture. Each finished culture broth contained 1.7–1.8 g of 2KGA. The time requirement in each fermentation cycle is given in Table 6.

TABLE 6

| Fermentation Cycle Number | Time (hr) | | | |
|---|---|---|---|---|
| | A | B | C | D |
| First | 28 | 28 | 28 | 28 |
| Second | 14 | 12 | 12 | 12 |
| Third | 14 | 13 | 12 | 13 |
| Fourth | 15 | 13 | 13 | 13 |

EXAMPLE 2

First fermentation was conducted by pure culture without using the concomitant bacterium. The fermentation medium used was prepared by adding 5 g/l of dry yeast to the composition shown in Table 4. The other aspects were the same as in Example 1. After the second cycle, recycling culture was conducted using the same recycling medium as in Example 1. The time requirement in each fermentation cycle is given in Table 7. Each finished culture broth contained 1.7–1.8 g of 2KGA.

TABLE 7

| Fermentation Cycle Number | Time (hr) | | | |
|---|---|---|---|---|
| | A | B | C | D |
| First | 30 | 30 | 30 | 30 |
| Second | 15 | 13 | 12 | 13 |
| Third | 16 | 13 | 13 | 12 |
| Fourth | 16 | 14 | 13 | 13 |

EXAMPLE 3

20 ml of seed medium A, having the composition shown in Table 2, was placed in a 200 ml conical flask, and sterilized at 120° C. for 20 minutes. To this flask, one loopful of cells of *Pseudogluconobacter saccharoketogenes* TH14-86 strain (IFO 14466, FERM BP-1128), grown at 30° C. for 3 days on a slant medium of the composition shown in Table 1, was inoculated, followed by shaking culture at 28° C. for 1 day, to yield a first seed culture broth. Similarly, two 1-liter conical flasks, each containing 200 ml of seed medium A, were sterilized. To each flask, 10 ml of the first seed culture broth was inoculated, followed by shaking culture at 28° C. for 2 days, to yield a second culture broth. To a sterilized 200 ml conical flask containing 20 ml of seed medium B shown in Table 3, one loopful of cells of the concomitant bacterium, grown on a slant medium of the composition shown in Table 1, was inoculated, followed by shaking culture at 28° C. for 2 days, to yield a seed culture broth of the concomitant bacterium.

To 30 g of L-sorbose, 60 g of CSL, 3 g of $FeSO_4$, 9 g of ammonium sulfate, 3 mg of vitamin $B_2$, 1.5 g of sucrose and 0.5 g of Actcol (produced by Takeda Chemical Industries), tap water was added to 1,660 ml. After adjustment to pH 7 with NaOH, this mixture was sterilized to yield a main fermentation medium. To this medium, 300 ml of the second culture broth of the oxidizing bacterium and 4 ml of the seed culture broth of the concomitant bacterium were added, and 0.3 g of lanthanum chloride in solution in 10 ml of water, previously sterilized, was added. A hollow fiber membrane filter (Microsa PMP-102®, produced by Asahi Chemical Industry) (previously sterilized with 0.5% NaOH) and a peristaltic pump were attached to a sterilized 5 liter jar fermentor. The above medium was placed in this fermentor; fermentation was initiated at a temperature of 32° C., an agitation speed of 800 rpm and an aeration rate of.0.5 vvm. The peristaltic pump, connected to a pH sensor, was operated to automatically add a 10N aqueous NaOH solution, to maintain pH 6.2. Separately, 270 g of L-sorbose was dissolved in tap water to 760 ml. After sterilization, this solution was continuously added to the culture broth so that the L-sorbose concentration in the broth was about 10–30 mg/ml. As a result, a total of 300 g of sorbose was completely oxidized in 18 hours, resulting in accumulation of 283.4 g of 2KGA in the culture broth. Fermentation was stopped when all L-sorbose was consumed, and the above filter was operated immediately. 2,700 ml of the filtrate, containing 2KGA, was removed from the system; when the amount of cell suspension in the fermentor was 300 ml, operation was stopped. 1,680 ml of a previously sterilized recycling medium D and separately sterilized 30 g of L-sorbose (84 ml) were added to the fermentor. Second fermentation was initiated under the same conditions as for the first fermentation. A solution of 270 g of L-sorbose in 760 ml of tap water was added in the same manner as in the first fermentation. This fermentation was repeated in 10 cycles. It took not more than 1 hour from completion of fermentation to initiation of the next cycle of fermentation, including filtering operation time. The time requirement and amount of 2KGA accumulated in each fermentation cycle are shown in Table 8.

TABLE 8

| Fermentation Cycle Number | Time (hr) | Amount (g) of 2KGA Accumulated |
|---|---|---|
| 1 | 18 | 274.5 |
| 2 | 11.5 | 290.7 |
| 3 | 10.5 | 298.2 |
| 4 | 10.5 | 291.9 |
| 5 | 11 | 297.6 |
| 6 | 12.5 | 288.9 |
| 7 | 14 | 272.6 |
| 8 | 15 | 286.8 |
| 9 | 16 | 285.0 |
| 10 | 16 | 271.8 |

EXAMPLE 4

Cells of *Bacillus megaterium* (IFO 12108), grown on the slant medium shown in Table 1 at 28° C. for 2 days, were suspended in 10 ml of sterile water. The entire amount was inoculated to a 2 liter Sakaguchi flask containing 500 ml of the seed medium sterilized previously shown in Table 3, followed by shaking culture at 28° C. for 2 days, to yield a seed culture broth of the concomitant bacterium. 30 l of the medium shown in Table 3 (pH 7.0) was added to a 50 liter fermentor, and sterilized with steam at 125° C. for 20 minutes. To this fermentor, 500 ml of the seed culture broth of *Bacillus megaterium* was added, followed by 4 days of culture at an agitation speed of 200 rpm, an aeration rate of 24 l/min, a pressure of 1.0 kg/cm$^2$G and a temperature of 28° C. The obtained culture broth was sterilized with steam at 120° C. for 20 minutes, and then stored in a cold place, which was then used as a component of the culture medium as a sterilized *Bacillus megaterium* culture broth (hereinafter also referred to as the mega broth).

500 ml of the seed culture medium shown in Table 2 was dispensed to a 2 liter Sakaguchi flask, and sterilized with steam at 120° C. for 20 minutes. One slant of cells of *Pseudogluconobacter saccharoketogenes*, TH14-86 strain, grown on the slant medium shown in Table 1 at 28° C. for 3 days, was inoculated to the above Sakaguchi flask, followed by shaking culture at 30° C. for 2 days. The obtained culture broth was transferred to a sterilized 50 liter fermentor containing 30 l of a seed medium consisting of 2.0% of D-glucose, 3.0% (v/v) of the mega broth, 1.0% of CSL, 0.5% of yeast extract, 0.1% of peptone, 0.3% of ammonium sulfate and 2.0% of calcium carbonate (Shiraishi Calcium Kaisha, Ltd.), followed by 48 hours of culture at a temperature of 32° C., an agitation speed of 150 rpm, an aeration rate of 15 l/min and a pressure of 1.0 kg/cm$^2$G, to yield a second culture broth of TH14-86 strain. Separately, 500 ml of the seed medium shown in Table 3 was dispensed to a 2 liter Sakaguchi flask, and sterilized with steam at 120° C. for 20 minutes. To this flask, cells of the concomitant bacterium *Bacillus megaterium* (IFO 12108), grown on the slant medium shown in Table 1, was transferred, followed by 48 hours of shaking culture at 28° C., to yield a seed culture broth of the concomitant bacterium. An aqueous solution of 80 l of the fermentation medium shown in Table 4 was added to a 200 l fermentor, and sterilized with steam at 125° C. for 20 minutes, after which 2 kg of L-sorbose (5 l), previously sterilized, 14 l of the second seed culture broth of the oxidizing bacterium as obtained above, and 500 ml of the seed culture broth of the concomitant bacterium were added to the fermentor; the mixture was filled to a final volume of 100 l.

Fermentation was started at an agitation speed of 120 rpm, an aeration rate of 70 l/min, a pressure of 1.0 kg/cm$^2$G and a temperature of 32° C. Separately, 30 l of a separately aseptically prepared aqueous solution containing 12 kg of L-sorbose was continuously added so that the L-sorbose (30 l) concentration in the culture broth in the fermentor was between 10 and 30 mg/ml. A 10N aqueous NaOH solution was added to maintain pH 6.2 for the culture broth. By 16 hours after fermentation initiation, the entire amount of L-sorbose was consumed, resulting in accumulation of 13.09 kg of 2KGA. After fermentation was stopped, the culture broth was filtered through a hollow fiber membrane filter (PMW302, Asahi Chemical Industry) which was sterilizeed with 0.5% NaOH, previously attached to the fermentor; the cell-containing fraction was concentrated to 14 l. The filtrate containing 2KGA was removed from the system; the concentrated cells were returned to the fermentor. 80 l of the recycling medium A, previously sterilized, and 2 kg of L-sorbose (5 l), separately sterilized, were added to the fermentor; the second fermentation was started under the same conditions as in the first fermentation. 12 kg of an aqueous L-sorbose solution (30 l) was continuously added from fermentation initiation. This fermentation was repeated in 4 cycles. The time requirement and amount of 2KGA accumulated in each fermentation cycle are shown in Table 9.

TABLE 9

| Fermentation Cycle Number | Time (hr) | 2KGA (kg) |
|---|---|---|
| First | 16 | 13.0 |
| Second | 12 | 13.8 |
| Third | 10 | 13.7 |
| Fourth | 11 | 14.0 |

EXAMPLE 5

Fermentation was conducted in the same manner as in Example 4, except that the recycling medium was replaced with medium C, and the filter was replaced with a ceramic membrane sterilized with steam (NGK Insulators, Ltd.). The time requirement and amount of 2KGA accumulated in each fermentation cycle are shown in Table 10.

TABLE 10

| Fermentation Cycle Number | Time (hr) | 2KGA (kg) |
|---|---|---|
| First | 16 | 12.7 |
| Second | 11 | 13.7 |
| Third | 12 | 14.1 |
| Fourth | 13 | 14.0 |

EXAMPLE 6

Fermentation was conducted in the same manner as in Example 4, except that the recycling medium was replaced with medium D, and the filter was replaced with a continuous centrifuge sterilized with steam (BTPX205 ALFALAVAL). The time requirement and amount of 2KGA accumulated in each fermentation cycle are shown in Table 11.

TABLE 11

| Fermentation Cycle Number | Time (hr) | 2KGA (kg) |
|---|---|---|
| First | 16 | 13.1 |
| Second | 11 | 14.4 |
| Third | 10 | 14.0 |
| Fourth | 12 | 14.3 |

EXAMPLE 7

Fermentation was conducted in the same manner as in Example 1 to obtain a first culture broth. A 25%, 50%, 75%, or 100% amount of this culture broth was centrifuged, and then used for recycling culture. The recycling medium used was medium D. The other aspects were the same as in Example 1. This fermentation was repeated in 4 cycles. The time requirements for completion of fermentation are shown in Table 12.

TABLE 12

| Fermentation Cycle Number | Time (hr) | | | |
|---|---|---|---|---|
| | 25% | 50% | 75% | 100% |
| First | 28 | 28 | 28 | 28 |
| Second | 22 | 16 | 12 | 13 |
| Third | 22 | 16 | 12 | 12 |
| Fourth | 23 | 18 | 13 | 12 |

We claim:

1. A method for producing 2-keto-L-gulonic acid which comprises
   (1) culturing a *Pseudogluconobacter saccharoketogenes* microorganism capable of producing 2-keto-L-gulonic acid from L-sorbose without immobilization, and with another microorganism capable of supplying a growth factor to the *Pseudogluconobacter saccharoketogenes*, in a liquid culture medium containing L-sorbose as a substrate and producing 2-keto-L-gulonic acid,
   (2) recovering the produced 2-keto-L-gulonic acid, while recovering the microorganism in the culture broth,
   (3) inoculating the recovered microorganism to a new sterilized liquid culture medium comprising L-sorbose, sucrose, ammonium sulfate, and optionally urea, and at least one cell reactivity retention aid selected from the group consisting of yeast extract, dry yeast and corn steep liquor, and,
   (4) repeating the steps (2) and (3) at least once.

2. The method of claim 1, wherein the microorganism capable of producing 2-keto-L-gulonic acid is selected from the group consisting of *Pseudogluconobacter saccharoketogenes* K591s (FERM BP-1130), *Pseudogluconobacter saccharoketogenes* TH14-86 (FERM BP-1128), *Pseudogluconobacter saccharoketogenes* 12-5 (FERM BP-1129), *Pseudogluconobacter saccharoketogenes* 12-15 (FERM BP-1132), *Pseudogluconobacter saccharoketogenes* 12-4 (FERM BP-1131), and *Pseudogluconobacter saccharoketogenes* 22-3 (FERM BP-1133).

3. The method of claim 1, wherein the microorganism capable of supplying a growth factor to the microorganism capable of producing 2-keto-L-gulonic acid from L-sorbose is selected from the group consisting of *Bacillus cereus* IFO 3131, *Bacillus licheniformis* IFO 12201, *Bacillus megaterium* IFO 12108, *Bacillus pumilus* IFO 12090, *Bacillus amyloliquefaciens* IFO 3022, *Bacillus subtilis* IFO 13719, *Bacillus circulans* IFO 3967, *Pseudomonas trifolii* IFO 12056, *Pseudomonas maltophilia* IFO 12692, *Proteus inconstans* IFO 12930, *Enterobacter cloacae* IFO 3320, *Erwinia herbicola* IFO 12686, *Xanthomonas pisi* IFO 13556, *Xanthomonas citri* IFO 3835 and *Flavobacterium menigosepticum* IFO 12535.

4. The method of claim 1, wherein the recovery of the microorganism of the step (2) is carried out by using a hollow fiber membrane filter, a ceramic membrane filter or a centrifuge.

5. The method of claim 1, wherein the recovery of the microorganism of the step (2) is carried out at 5° to 40° C.

* * * * *